United States Patent
Ohkoshi et al.

(10) Patent No.: US 7,102,029 B2
(45) Date of Patent: Sep. 5, 2006

(54) METHOD OF CRYSTALLIZATION

(75) Inventors: Fumio Ohkoshi, Okayama (JP); Takahisa Furuya, Okayama (JP)

(73) Assignees: Mitsubishi Gas Chemical Company, Inc., Tokyo (JP); Toyo Boseki Kabushiki Kaisha, Osaka (JP); Mizushima Aroma Company, Ltd., Kurashiki (JP)

( * ) Notice: Subject to any disclaimer, the term of this patent is extended or adjusted under 35 U.S.C. 154(b) by 0 days.

(21) Appl. No.: 10/398,191

(22) PCT Filed: Sep. 21, 2001

(86) PCT No.: PCT/JP01/08237

§ 371 (c)(1),
(2), (4) Date: Apr. 2, 2003

(87) PCT Pub. No.: WO02/28499

PCT Pub. Date: Apr. 11, 2002

(65) Prior Publication Data

US 2004/0093697 A1    May 20, 2004

(30) Foreign Application Priority Data

Oct. 2, 2000 (JP) ............................ 2000-301776

(51) Int. Cl.
C07C 51/42 (2006.01)

(52) U.S. Cl. ..................................... 562/486; 562/485

(58) Field of Classification Search ................ 562/485, 562/486

See application file for complete search history.

(56) References Cited

U.S. PATENT DOCUMENTS 2,794,832 A * 6/1957 Rietema ..................... 562/486
4,707,274 A 11/1987 Donhauser et al.
5,705,682 A 1/1998 Ohkoshi et al.
5,973,196 A 10/1999 Takano et al.

FOREIGN PATENT DOCUMENTS

| EP | 0 818 433 A2 | 1/1998 |
|---|---|---|
| JP | 8-208561 | 8/1996 |
| JP | 10195016 | * 7/1998 |
| JP | 11-335321 | 12/1999 |
| WO | WO 98/38150 | 9/1998 |

OTHER PUBLICATIONS

International Search Report mailed Jan. 15, 2002.
Supplementary European Search Report, for Application No. EP 01 96 7778, dated May 19, 2005.

* cited by examiner

*Primary Examiner*—Taylor Victor Oh
(74) *Attorney, Agent, or Firm*—Antonelli, Terry, Stout and Kraus, LLP.

(57) ABSTRACT

The present invention proposes a crystallization process comprising the steps of feeding a slurry solution in which a terephthalic acid solution or a part of the terephthalic acid is precipitated to a crystallization vessel, precipitating the terephthalic acid in the crystallization vessel, generating a slurry containing crystals and solvent, discharging the slurry, and further comprising the steps of introducing the slurry in a tangential direction of a hydrocyclone, returning the slurry flowing out as a downward swirling flow from a lower part of the hydrocyclone to the vessel, and discharging the slurry overflowing from the upper part of the hydrocyclone. According to the present invention, crystals of large particle size is obtained and a stable driving ranging long term can be achieved because any adhesion or accumulation of the terephthalic acid crystals does not appear at all in the crystallization vessel.

15 Claims, 1 Drawing Sheet

METHOD OF CRYSTALLIZATION

TECHNICAL FIELD

The present invention relates to a crystallization process, in which a slurry solution of terephthalic acid is fed to a crystallization vessel, where the terephthalic acid is precipitated and the slurry including crystals and a solvent (mother liquor) is discharged. More particularly, the present invention is employed for separation, etc. of purified terephthalic acid crystals.

BACKGROUND ART

The purified terephthalic acid is produced by oxidizing paraxylene with a molecular oxygen in liquid phase, dissolving a crude product of terephthalic acid in hot water, and catalytically hydrogenating the aqueous solution of the crude terephthalic acid by contacting with a catalyst of noble metal belonging to the group VIII of the Periodic table in the presence of hydrogen. This production process employing an apparatus of commercial scale has a production performance ranging many years.

In this process, the slurry prepared by cooling the hydrogenated reaction liquid and including the precipitated terephthalic acid crystals is separated to the first crystallization products and the first mother liquor product usually at the temperature of from 120° C. to 220° C. The first mother liquor product contains considerable amounts of dissolved impurities such as paratoluic acid being a hydrogenated product of 4-carboxybenzaldehyde (4CBA), which is a main impurity in the crude terephthalic acid, the terephthalic acid corresponding to the solubility of the isolation temperature and other impurities, etc. Further, it may contain small amounts of the terephthalic acid crystals.

Mere disposal of the first mother liquor product significantly increases the load of an effluent treatment. Further, it is rational that the paratoluic acid and the terephthalic acid are recovered as the second crystallization products and reused because the paratoluic acid is a precursor of the terephthalic acid. The production of the purified terephthalic acid containing recovery and return of the second crystallization products to the liquid phase oxidation process is described in Japanese Examined KOKOKU Patent Publication No. Shou 56-35174 and Japanese Laid-Open Patent Publication No. Hei 10-195016, etc.

Additionally, Japanese Laid-Open Patent Publication No. Hei 8-231465 discloses a mother liquor substitution method for dividing terephthalic acid crystal particles instead of using elevated pressure centrifugal separation method.

Regarding the recovery of the second crystallization products to the liquid phase oxidation process, the foregoing Japanese Examined KOKOKU Patent Publication No. Shou 56-35174 further teaches that "The crystallization temperature of the second crystallization products should be 130° C. to 100° C.". Further, Japanese Laid-Open Patent Publication No. Hei 10-195016 teaches that "The raw water solvent discharged is subsequently cooled to 40° C. or less by decompression.".

According to the experiences of the inventors ranging many years, however, when the slurry with comparatively low concentration of the crystals is generated in a crystallization vessel as the case of recovering the second crystallization products, crystals are easy to accumulate on the inner wall and the internal structure of the crystallization vessel. Further, when the concentration of the crystals in the crystallization vessel is low, a stable separating operation in downstream tends to become difficult in many cases because the particle sizes of the crystals relatively decrease.

In other words, the inventors tried to introduce the first mother liquor product separated at the temperature of about 145° C. into a crystallization vessel in the above-mentioned purified terephthalic acid preparing apparatus, to cool down to 100° C. with flash vaporization of a solvent (water), and to supply the generated slurry to a separating means for the second crystallization products, the internal structure of the crystallization vessel was found to be adhered and accumulated by the crystals. Furthermore, the pressurized filtration method selected as separating means was found to induce an intense blocking of a filter, and frequent cleanings of the filter with short intervals were necessary.

It is an object of the present invention to provide a way of long and stable operation of the crystallization vessel and the separating means of the crystals in the process of feeding the slurry solution of terephthalic acid to the crystallization vessel, precipitating the terephthalic acid in the crystallization vessel, generating and discharging the slurry including crystals and solvent.

DISCLOSURE OF THE INVENTION

As the result of intensive extensive research and investigation about the approach for recovering the second crystallization products in purified terephthalic acid preparation apparatus accumulated by the present inventors, it has been found that the above-mentioned object is achieved by installing a hydrocyclone between the crystallization vessel and the separating means. It has also been found that, by the installation of the hydrocyclone, the particle size of the crystals in the crystallization vessel increases. Further, by reversing an ordinary flow in the hydrocyclone, i.e. by reversing the exhaust current that discharges a downward swirling flow down to the separating means, and by discharging the overflow from upper part of the hydrocyclone after returning the downward swirling flow to the crystallization vessel, adhesion pile of the crystals on the crystallization vessel is found to be completely prevented without causing blocking of filter in the separation of the crystals. Such being the case, the present invention has been accomplished on the basis of the foregoing findings and information.

The present invention is a crystallization process comprising the steps of feeding a slurry solution in which a terephthalic acid solution or a part of the terephthalic acid is precipitated to a crystallization vessel, precipitating the terephthalic acid in the crystallization vessel, generating a slurry containing crystals and solvent, discharging the slurry, and further comprising the steps of introducing the slurry in a tangential direction of a hydrocyclone, returning the slurry flowing out as a downward swirling flow from a lower part of the hydrocyclone to the crystallization vessel, and discharging the slurry overflowing from the upper part of the hydrocyclone.

Specifically, the present invention is employed for a crystallization process comprising the steps of dissolving a crude product of terephthalic acid obtained by oxidizing paraxylene with a molecular oxygen in liquid phase into hot water, catalytically hydrogenating the aqueous solution of the crude terephthalic acid by contacting with a catalyst of a noble metal belonging to the group VIII of the Periodic table in the presence of hydrogen, thereafter cooling the resultant solution, feeding the first mother liquor product crystallizingly separated most of the terephthalic acid as the first crystallization products to the crystallization vessel, supplying the slurry including the second crystallization products obtained in the crystallization vessel by further cooling the mother liquor product to a separating means, and recovering the second crystallization products.

EXPLANATIONS OF NUMERICAL SYMBOLS

Figure 1:
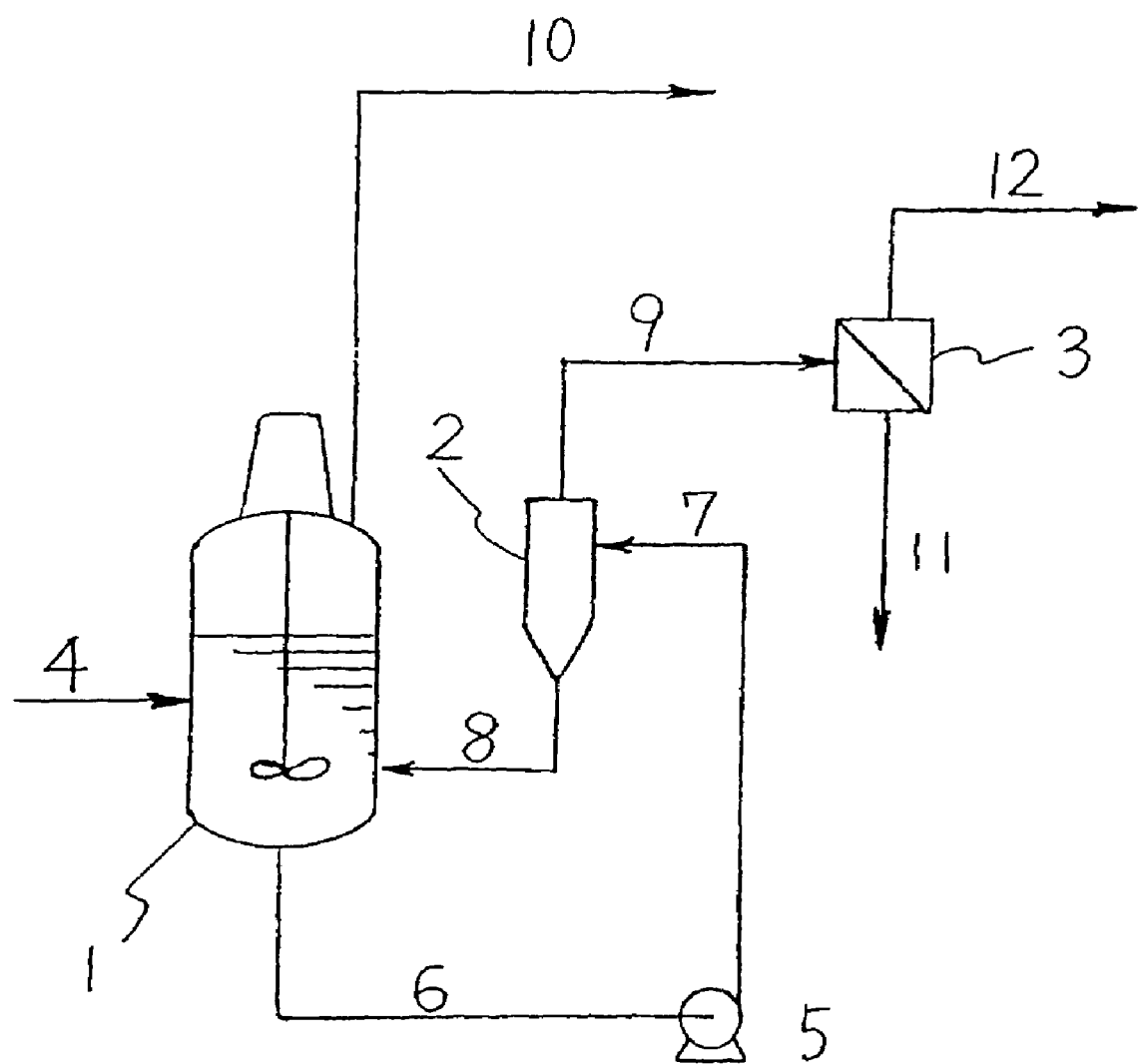
FIG. 1 is a system diagram showing an embodiment of a crystallization process in accordance with the present invention and illustrating a treatment process of the first mother liquor product employed to the separation for the second crystallization products in the preparation of a purified terephthalic acid.

In FIG. 1, numerical symbol 1 shows a crystallization vessel, numerical symbol 2 shows a hydrocyclone, numerical symbol 3 shows a crystal separating means, and numerical symbol 5 shows a slurry-circulating pump.

THE MOST PREFERRED EMBODIMENT TO CARRY OUT THE INVENTION

The following is an explanation of an embodiment of the present invention producing a purified terephthalic acid from paraxylene as ingredients.

Liquid phase oxidation reaction of the paraxylene is conducted in a solvent of acetic acid containing water with the existence of a heavy metal and bromine as catalysts. Cobalt and manganese are usually employed as the heavy metal, and there is a case of addition of the other components such as chromium or iron. Air is generally employed as the oxidizing agent, and an oxygen enriched air obtained by mixing oxygen gas in the air or, on the contrary, the air lowering the oxygen concentration by mixing nitrogen, etc. is also employed as the oxidizing agent. The reaction temperature is from 170° C. to 220° C. The oxidation reaction may be conducted as a multisteps reaction with two or more steps. The oxidation reaction products are, essentially, cooled through series coupled crystalliser vessel of at least one step, separating the terephthalic acid crystals precipitated, dried by a dryer and provided as a crude terephthalic acid. The crude terephthalic acid is fed into a purification system and purified thereby obtaining a purified terephthalic acid.

In the purification system, the crude terephthalic acid is dissolved in hot water and is supplied to a hydrogenation column as the aqueous solution of 20% to 35%.

Inside the hydrogenation column, catalysts of noble metal belonging to the group VIII of the Periodic table are filled and impurities in the crude terephthalic acid are hydrogenated by supplying hydrogen. Platinum, palladium, rhodium, ruthenium, etc. are employed as the noble metal catalyst belonging to the group VIII of the Periodic table, and the catalyst provided by supporting palladium on activated carbons is particularly effective. The catalyst blending at least two kinds of the foregoing metals may be employed. Coconut shell charcoal is effective as the activated carbon.

Regarding the supplying amounts of the hydrogen, although it is generally appropriate to be approximately 2 times of required amounts for reducing the 4-carboxybenzaldehyde (4CBA) as a main impurity in the crude terephthalic acid to paratoluic acid, it is necessary to adjust considering the amounts of the impurities that can be reduced. The hydrogenation reaction temperature is in the range of from 250° C. to 330° C., and it is particularly suitable to be from 270° C. to 300° C. The hydrogenation reaction time is suitable to be in the range of from 2 minutes to 20 minutes.

The reaction products discharged from the hydrogenation column are fed to the crystalliser vessel through a filter installed essentially with an object of preventing the flowing out of minute debris of the catalyst, etc.

The crystalliser vessel is coupled at least one step in series and the filtered reaction products are sequentially cooled in each step by means of flash vaporization of the water as the solvent, thereby providing a slurry containing precipitated crystals of the terephthalic acid dissolved in the reaction products.

After cooling the slurry down to the temperature of from 120° C. to 220° C., preferably to the temperature of from 130° C. to 200° C., the cooled slurry is supplied to separating means, where the cooled slurry is separated into the first crystallization products and the first mother liquor product.

With regards to the separating means, although various methods are employed, a centrifugal separation method is adaptive because it has a practical performance in commercial scale ranging for many years. However, the centrifugal separation method cannot evade the operation under the elevated pressure because it is the separation method at the temperature far over the boiling point of the water under the ordinary pressure. The cost required for the investment and maintenance of an elevated pressure centrifugal separator is very expensive.

As a prior art, Japanese Laid-Open Patent No. Hei 8-231465 proposes mother liquor substitution method as alternative for the elevated pressure centrifugal separation method and in this case, raw slurry and fresh water are fed from the upper part and the lower part of a mother liquor substitution column respectively. Crystals subside freely in the mother liquor substitution column and solvent of the raw slurry, the first mother liquor product, is discharged from the top of the column, a slurry dissolved in the fresh water as a replaced solvent being drawn out from the bottom of the column.

In comparison with the elevated pressure centrifugal separation method, the mother liquor substitution method has many advantages in that investment is markedly small, that it is free from maintenance because of having almost no operating mechanism, that the substitution rate between the mother liquor and the fresh water can be controlled easily and that it can be driven even at elevated temperature without limitation, etc.

The first crystallization products of the terephthalic acid obtained by the separating means are dispersed again optionally in the fresh water and crystals containing water are obtained by passing the dispersed solution through the separating means again in the centrifugal separation method. The crystals containing water are made into purified terephthalic acid products by being dried with a dryer. In the mother liquor substitution method, crystals containing water are obtained from the slurry in which the first mother liquor product is replaced to fresh water by passing the slurry through the separating means again and they are made into purified terephthalic acid products by being dried with a dryer.

The first mother liquor product obtained by the separating means at elevated temperature is fed to the crystallization vessel and is cooled by flash vaporization or other means, and the second slurry including the second crystallization products is provided by the crystallization of the terephthalic acid dissolved in the first mother liquor product. The second slurry is cooled down further on its necessity and finally, the second crystallization products are recovered by passing the slurry through the separating means.

The gist of the present invention reside in introducing the second slurry discharged from the crystallization vessel into tangential direction of the hydrocyclone, returning the slurry flowing out as a downward swirling flow from the lower outlet of the hydrocyclone to the crystallization vessel and supplying the slurry overflowing from the upper outlet of the hydrocyclone to another separating means for the second crystallization products.

In the case where the slurry is directly supplied to the separating means without passing through the hydrocyclone, a stable driving ranging long term is difficult, as will be described in Comparative Example 1 below, because terephthalic acid crystals adhere and accumulate on the inner wall and internal structure of the crystallization vessel.

Further, even in the case where the slurry is supplied to the separating means passing through the hydrocyclone, the original flow of the hydrocyclone supplying the downward swirling flow to the separating means and returning the overflow into the crystallization vessel does not show any effects, as will be described in Comparative Example 2 below, in the prevention of adhesion and accumulation of the terephthalic acid crystals on the inner wall and internal structure of the crystallization vessel.

In accordance with the present invention, however, by introducing the slurry drawn out from the crystallization vessel into an inlet of the hydrocyclone in the tangential direction of itself, returning the slurry flowing out as a downward swirling flow from the lower outlet of the hydrocyclone to the crystallization vessel and discharging the slurry overflowing from the upper outlet of the hydrocyclone, a stable driving ranging long term can be achieved because any adhesion or accumulation of the terephthalic acid crystals does not appear at all. Although the reason why the foregoing effect generates is not clear, it is estimated as the following.

An installation of the hydrocyclone in accordance with the present invention remarkably increases the concentration of the slurry in the crystallization vessel. For example, although the concentration of the slurry in the crystallization vessel was 0.3% or less both in Comparative Example 1 without the installation of the hydrocyclone and in Comparative Example 2 that employed the hydrocyclone with original flow, the concentration of the slurry in the crystallization vessel was as large as about 10% in Example 1 of the present invention. Additionally, the average particle diameter of the crystal products was remarkably as large as 120 μm in accordance with the present invention.

By returning the slurry flowing out as a downward swirling flow from the lower outlet of the hydrocyclone to the crystallization vessel in accordance with the present invention, the crystals once adhered to the inner wall and inside structure of the vessel are presumed to be scraped down by the crystals of large particle diameter induced by the increase of the concentration of the slurry in the crystallization vessel.

According to the present invention, separation of the second crystallization products in the latter steps become easy because particle sizes of the crystals in the slurry overflowing from the upper outlet of the hydrocyclone become extremely large.

In the present invention, there are not almost any limitation in the scale or the operating condition, for example, injection angle of the slurry, velocity, the flow velocity distribution, etc. in the hydrocyclone. Any adhesion or accumulation of the terephthalic acid crystals to the inner wall of the crystallization vessel, etc. will be effectively prevented on the assumption that the function inherent in the hydrocyclone is achieved to some extent.

Additionally, a kind of the hydrocyclone is not particularly limited, and any hydrocyclone of jet flush-in type or Dreasen type both of general-purpose is used preferably. Further, multi-steps of the hydrocyclone are installed in series.

The slurry overflowed from the upper outlet of the hydrocyclone is fed to the separating means after further precipitating the dissolved component by passing the slurry through an additional cooling process depending on the necessity.

In the separating means, the slurry is separated into the second mother liquor product and the second crystallization products by means of any separating methods of, for example, pressure filtration, centrifugal separation, etc. The second crystallization products are discharged to a process of reuse, and, as for the second mother liquor product, they are usually exhausted outside the apparatus via an effluent treatment process.

In the present invention, cooling by flash vaporization of solvent is desirable as the method of making the terephthalic acid precipitate from the slurry.

The concentration of the crystals in the slurry overflowing from the upper outlet of the hydrocyclone is preferably 5% or less, more preferably 1% or less.

For a better understanding of the present invention together with other objects, advantages and capabilities thereof, reference is made to the following description in connection with the drawings. FIG. 1 is an example of system diagram of a crystallization process according to the present invention illustrating a treating process of the first mother liquor product employed to the separation for the second crystallization products in the preparation of purified terephthalic acid.

In FIG. 1, the first mother liquor product (i.e. a solution or a slurry solution with partially precipitated solute) from the separating means at an elevated temperature is fed to the crystallization vessel 1 through feed pipe 4 for the first mother liquor product.

In crystallization vessel 1, the mother liquor is cooled down by flash vaporization and a slurry containing crystals of crystallized terephthalic acid is provided. The vapor generated in the crystallization vessel is exhausted outside the vessel through flash vapor exhaust pipe 10.

The slurry provided in crystallization vessel 1 is drawn out through line 6, and is introduced into introduction inlet 7 in tangential direction of hydrocyclone 2 by means of slurry circulating pump 5.

The downward swirling flow generated in hydrocyclone 2 is returned to crystallization vessel 1 through line 8. Rising overflow in the hydrocyclone is supplied to crystal separating means 3 through line 9.

The general-purpose separating method such as pressure filtration method or centrifugal separation method is employed as crystal separating means 3, where the slurry is separated into the second crystallization products and the second mother liquor product.

The second crystallization products are drawn out through line 11 and are discharged to recycling process. The second mother products are drawn out through line 12 and are routed to an effluent treatment process.

The present invention is broadly adaptive for the process accompanied by crystallization and separation, and makes the crystal separating operation in the following step easy because the crystals with a large particle size can be obtained.

As will be described in the Example below, by introducing the slurry drawn out from the crystallization vessel into an inlet of the hydrocyclone in the tangential direction of itself, returning the slurry flowing out as a downward swirling flow from the lower outlet of the hydrocyclone to the crystallization vessel and discharging the slurry overflowing from the upper outlet of the hydrocyclone, in accordance with the present invention, a stable driving ranging long term can be achieved because any adhesion or accumulation of the terephthalic acid crystals does not appear at all induced by the generation of crystals with extremely large crystal particle sizes.

EXAMPLES

In the following examples are described several preferred embodiments to concretely illustrate the invention, however, it is to be understood that the invention is not intended to be limited to the specific embodiments.

Example 1

In an apparatus for producing purified terephthalic acid by catalytic hydrogenation process dissolving the crude terephthalic acid obtained by liquid phase oxidation of paraxylene in water, a crystallization operation of the first mother liquor product obtained by mother liquor substitution method was conducted by the use of an apparatus shown as system diagram in FIG. 1.

By feeding the first mother liquor product with the temperature of 145° C. obtained by mother liquor substitution method to crystallization vessel 1 through feed pipe 4 for the first mother liquor product, the operation was conducted in accordance with the system diagram. The supplying amount of the first mother liquor product to crystallization vessel 1 was 100 parts of water, 0.3 parts of terephthalic acid, which partially exist as crystals, respectively. Almost all other impurities were dissolved in water.

In crystallization vessel 1, the first mother liquor product was cooled down to 100° C. by flash vaporization of water and a slurry containing crystals by crystallization of dissolved terephthalic acid was obtained.

The slurry was drawn out and introduced into introduction inlet 7 in the tangential direction of jet flush-in type hydrocyclone 2 by means of slurry circulating pump 5. About 33 parts of water and accompanied crystals were drawn out through downward swirling flow outlet 8 and were returned to crystallization vessel 1. From the upper overflow outlet 9, the slurry with the temperature of 100° C. was drawn out. The concentration of the crystals among the slurry in line 6 was a little over 10%. An averaged particle diameter of the crystals was about 120 μm.

The second crystallization products were recovered from the slurry with the temperature of 100° C. flown out from the upper overflow outlet 9 by means of the alteration operation of two pressure filters employed as the separating means and were discharged to oxidation reaction process through line 11. Further, the second mother liquor product separated from the slurry were drawn out through line 12 and routed to an effluent treatment process.

Continuous operation ranging about half a year of the foregoing steps in succession did not cause any problems at all.

Comparative Example 1

The operation similar to Example 1 was conducted without installing hydrocyclone 2. That is, the slurry with the temperature of 100° C. was drawn out from crystallization vessel 1 by pump 5 and after recovering the second crystallization products by means of the alteration operation of two pressure filters employed as the separating means, the operation discharged the second crystallization products to oxidation reaction process through line 11. Further, the second mother liquor product separated from the slurry were drawn out through line 12 and routed to the effluent treatment process.

At this time, an averaged particle diameter of the crystals in line 6 was about 20 μm. After the continuous operation ranged for 13 days, the slurry became impossible to be drawn out from crystallization vessel 1. By overhaul inspection of crystallization vessel 1, the inner wall and the internal structure of the crystallization vessel were found to be adhered by the crystals. Further, the crystals accumulated over the bottom of the vessel. Furthermore, the cleanings of the filters with intervals of about 2 days were necessary for the continuous operation of the pressure filters.

Comparative Example 2

In Example 1, 33 parts of water overflowed from the upper overflow outlet 9 of jet flush-in type hydrocyclone 2 with the accompanying crystals were returned to crystallization vessel 1 thereby supplying the slurry drawn out from the downward swirling flow outlet 8 to separating means 3 provided in downstream side of crystallizes vessel 1. The concentration of the crystals among the slurry in line 6 was a little over 0.2% and an average particle diameter of the crystals was about 70 μm.

The second crystallization products were recovered from the slurry with the temperature of 100° C. drawn out from the downward swirling flow outlet 8 by means of the alteration operation of two pressure filters employed as the separating means and were discharged to oxidation reaction process through line 11. Further, the second mother liquor product separated from the slurry was drawn out through line 12 and routed to the effluent treatment process.

After the continuous operation ranged for 11 days, the slurry became impossible to be drawn out from crystallization vessel 1. By overhaul inspection of crystallization vessel 1, the inner wall and the internal structure of the crystallizer vessel were found to be adhered by the crystals. Further, the crystals accumulated over the bottom of the vessel. Furthermore, the cleanings of the filters with intervals of about 2 days were necessary for the continuous operation of the pressure filters.

What is claimed is:

1. A crystallization process including the steps of feeding a terephthalic acid solution or a slurry solution in which a part of the terephthalic acid is precipitated to a crystallization vessel, precipitating the terephthalic acid in the crystallization vessel, generating a slurry containing crystals and solvent, and discharging the slurry, and comprising the further steps of:
   (i) introducing the slurry discharged from the crystallization vessel to a hydrocyclone, in a tangential direction of the hydrocyclone,
   (ii) returning all amount of the concentrated slurry flowing out as a downward swirling flow from a lower part of the hydrocyclone directly to the crystallization vessel, and
   (iii) discharging the slurry overflowing from an upper part of the hydrocyclone, wherein the concentration of crystals in said slurry overflowing from said upper part of said hydrocyclone is 5% or less.

2. The crystallization process according to claim 1, wherein said precipitating the terephthalic acid in the crystallization vessel is conducted with cooling by flash vaporization of solvent.

3. The crystallization process according to claim 2, wherein crystals and mother liquor product are separated from each other after supplying said slurry overflowing from the upper part of said hydrocyclone to a separating means.

4. The crystallization process according to claim 1, wherein, prior to the feeding of the terephthalic acid solution or the slurry solution in which the part of the terephthalic acid is precipitated to the crystallization vessel, the process further comprises the steps of:
dissolving a crude product of terephthalic acid obtained by oxidizing paraxylene with a molecular oxygen in liquid phase in hot water, thereby forming an aqueous solution of crude terephthalic acid, and
catalytically hydrogenating the aqueous solution of the crude terephthalic acid by contacting with group VIII noble metal catalyst in the presence of hydrogen, and thereafter cooling the resultant solution,
wherein a first mother liquor product in which most of the terephthalic acid has been separated as crystals as first crystallization products, is fed to said crystallization vessel, and
wherein second crystallization products are recovered from the slurry including second crystallization products obtained in the crystallization vessel by further cooling the mother liquor.

5. The crystallization process according to claim 4, wherein said slurry solution of terephthalic acid including the second crystallization products is provided by a mother liquor substitution method.

6. The crystallization process according to claim 1, wherein crystals and mother liquor product are separated from each other after supplying said slurry overflowing from the upper part of said hydrocyclone to a separating means.

7. The crystallization process according to claim 6, wherein, prior to the feeding of the terephthalic acid solution or the slurry solution in which the part of the terephthalic acid is precipitated to the crystallization vessel, the process further comprises the steps of:
dissolving a crude product of terephthalic acid obtained by oxidizing paraxylene with a molecular oxygen in liquid phase in hot water, thereby forming an aqueous solution of crude terephthalic acid, and
catalytically hydrogenating the aqueous solution of the crude terephthalic acid by contacting with group VIII noble metal catalyst in the presence of hydrogen, and thereafter cooling the resultant solution,
wherein a first mother liquor product in which most of the terephthalic acid has been separated as crystals as first crystallization products, is fed to said crystallization vessel, and
wherein second crystallization products are recovered from the slurry including second crystallization products obtained in the crystallization vessel by further cooling the mother liquor.

8. The crystallization process according to claim 7, wherein said slurry solution of terephthalic acid including the second crystallization products is provided by a mother liquor substitution method.

9. The crystallization process according to claim 3, wherein, prior to the feeding of the terephthalic acid solution or the slurry solution in which the part of the terephthalic acid is precipitated to the crystallization vessel, the process further comprises the steps of:
dissolving a crude product of terephthalic acid obtained by oxidizing paraxylene with a molecular oxygen in liquid phase in hot water, thereby forming an aqueous solution of crude terephthalic acid, and
catalytically hydrogenating the aqueous solution of the crude terephthalic acid by contacting with group VIII noble metal catalyst in the presence of hydrogen, and thereafter cooling the resultant solution,
wherein a first mother liquor product in which most of the terephthalic acid has been separated as crystals as first crystallization products, is fed to said crystallization vessel, and
wherein second crystallization products are recovered from the slurry including second crystallization products obtained in the crystallization vessel by further cooling the mother liquor.

10. The crystallization process according to claim 9, wherein said slurry solution of terephthalic acid including the second crystallization products is provided by a mother liquor substitution method.

11. The crystallization process according to claim 2, wherein, prior to the feeding of the terephthalic acid solution or the slurry solution in which the part of the terephthalic acid is precipitated to the crystallization vessel, the process further comprises the steps of:
dissolving a crude product of terephthalic acid obtained by oxidizing paraxylene with a molecular oxygen in liquid phase in hot water, thereby forming an aqueous solution of crude terephthalic acid, and
catalytically hydrogenating the aqueous solution of the crude terephthalic acid by contacting with group VIII noble metal catalyst in the presence of hydrogen, and thereafter cooling the resultant solution,
wherein a first mother liquor product in which most of the terephthalic acid has been separated as crystals as first crystallization products, is fed to said crystallization vessel, and
wherein second crystallization products are recovered from the slurry including second crystallization products obtained in the crystallization vessel by further cooling the mother liquor.

12. The crystallization process according to claim 11, wherein said slurry solution of terephthalic acid including the second crystallization products is provided by a mother liquor substitution method.

13. The crystallization process according to claim 3, wherein said slurry overflowing from the upper part of said hydrocyclone is passed through a cooling process and thereafter supplied to said separating means.

14. The crystallization process according to claim 3, wherein the concentration of crystals in said slurry overflowing from said upper outlet of said hydrocyclone is 1% or less.

15. A crystallization process including the steps of feeding a terephthalic acid solution or a slurry solution in which a part of the terephthalic acid is precipitated to a crystallization vessel, precipitating the terephthalic acid in the crystallization vessel, generating a slurry containing crystals and solvent, and discharging the slurry, and comprising the further steps of:

(i) introducing the slurry discharged from the crystallization vessel to a hydrocyclone, in a tangential direction of the hydrocyclone, (ii) returning the concentrated slurry flowing out as a downward swirling flow from a lower part of the hydrocyclone directly from the hydrocyclone to the crystallization vessel, and (iii) discharging the slurry overflowing from an upper part of the hydrocyclone, wherein the concentration of crystals in said slurry overflowing from said upper part of said hydrocyclone is 5% or less.

* * * * *